United States Patent [19]

Brown et al.

[11] Patent Number: 5,144,565
[45] Date of Patent: Sep. 1, 1992

[54] MEASUREMENT OF METALLURGICAL PROPERTIES IN FERROMAGNETIC TEST PARTS

[75] Inventors: Gordon R. Brown, Livonia; Thomas C. Targosz, Oak Park, both of Mich.

[73] Assignee: K. J. Law Engineers, Inc., Novi, Mich.

[21] Appl. No.: 499,980

[22] Filed: Mar. 26, 1990

[51] Int. Cl.[5] ............................................. G06F 15/20
[52] U.S. Cl. .................................................... 364/507
[58] Field of Search ............................... 364/507, 508

[56] References Cited

U.S. PATENT DOCUMENTS

| | | | |
|---|---|---|---|
| 4,507,740 | 3/1985 | Star et al. | 364/487 |
| 4,628,261 | 12/1986 | Hüschelrath et al. | 364/507 X |
| 4,630,229 | 12/1986 | D'Hondt | 364/726 |
| 4,631,688 | 12/1986 | Boehm et al. | 364/507 |
| 4,821,204 | 4/1989 | Hüschelrath | 364/507 X |

Primary Examiner—Parshotam S. Lall
Assistant Examiner—Edward R. Cosimano
Attorney, Agent, or Firm—Barnes, Kisselle, Raisch, Choate, Whittemore & Hulbert

[57] ABSTRACT

Apparatus for measuring metallurgical properties of a ferromagnetic test piece that includes a variable frequency oscillator for providing a periodic signal, and a test coil arrangement for applying the periodic signal to a test piece to generate eddy currents therein. A test signal is developed in response to eddy currents induced in the test piece and fed to a microprocessor-based digital controller. The digital controller is coupled to the oscillator for generating the oscillator periodic signal at successive first and second test frequencies. At least two harmonic components of the test signal are separated from each other by the digital controller at each test frequency. A plurality of constants empirically relating amplitude and phase characteristics of the harmonics to the desired material properties are prestored in the digital processor, and are employed in conjunction with amplitude and phase information of the separated harmonic components during a test operation using linear regression techniques for determining desired properties of the test piece.

23 Claims, 3 Drawing Sheets

MEASUREMENT OF METALLURGICAL PROPERTIES IN FERROMAGNETIC TEST PARTS

The present invention is directed to measurement of predetermined properties in workpieces or parts, and more particularly to a method and apparatus for measuring metallurgical properties in ferromagnetic test pieces.

BACKGROUND AND OBJECTS OF THE INVENTION

Nondestructive test techniques employing eddy current principles have been used for many years to measure or predict various metallurgical properties of ferrous and nonferrous metals. A periodic magnetic field is applied to a test part to induce eddy currents in the test part, and the amplitude and/or phase of signals induced by the eddy currents in a secondary coil is employed to measure or predict such properties as hardness, case depth, grinder burn, carbon burnout at the material surface, alloy separation and degree of heat treatment. It has also been recognized that, when such techniques are employed in conjunction with ferromagnetic test pieces, the nonlinear magnetization curve of the ferromagnetic material causes odd harmonic frequencies to appear in the output voltage of the secondary test coil. As disclosed in U.S. Pat. No. 4,630,229, amplitude and phase information of the various harmonics, developed by fourier transform or other suitable techniques, can be employed to identify and distinguish various metallurgical properties of the test pieces. Excitation of the test coils at multiple successive frequencies has been found useful to yield additional information on material properties Although eddy current test systems and methods of the described character have been successfully employed in the laboratory, improvements remain desirable. For example, instrumentation heretofore proposed has generally required operation by a skilled technician for manipulation of test parameters and interpretation of results, and therefore has not been well suited for use in a mass production environment for one hundred percent testing of many pieces per hour. Another disadvantage of prior art devices of the described character lies in general failure to take advantage of current electronic technology, particularly the memory and data manipulation capabilities of available microprocessors, to relieve the operator from the requirement of parameter manipulation and data interpretation during the test process A general object of the present invention, therefore, is to provide a method and apparatus for measuring properties of test materials, particularly metallurgical properties of ferromagnetic test pieces, that, by employing available digital microprocessor-based technology, are adapted for rapid and accurate measurement of desired properties, and thus are suitable for use by relatively unskilled personnel in the environment of a mass production manufacturing operation. Another and more specific object of the present invention is to provide a method and apparatus of the described character that may be preprogrammed with empirically derived data for controlling test parameters, and thereafter automatically execute a test sequence on successive workpieces without substantial operator intervention. A further object of the invention is to provide a method and apparatus of the described character in which the test parameters and control process may be readily modified or reprogrammed for accommodating changed conditions of the test pieces and/or use in conjunction with test pieces of differing properties. Yet another object of the present invention is to provide a system and method that employs eddy current techniques for measuring properties of test materials at multiple successive test frequencies and/or signal amplitudes in which frequency and/or amplitude change is closely controlled so as to eliminate ringing and generation of spurious harmonics in the secondary test coil, and thereby enhance both the speed and accuracy of the testing operation.

Yet another object of the present invention is to provide a method and apparatus of the described character that is adapted for testing and sorting workpieces that cannot be readily sorted employing conventional technology, such as cast or forged gears, bolts, spindles, camshafts and sprockets. Another and more specific object of the invention is to provide a method and apparatus for enhanced simultaneous sorting for multiple different metallurgical conditions, such as surface hardness, case depth, hardened zone location, material strength, etc. A further object of the invention is to provide a method and apparatus of the described character that employs high power for enhanced sorting of induction-hardened or carburized materials, that are user friendly, that are adapted for communication with industrial controllers or other management information systems for data downloading and statistical evaluation, and that are adapted for automatic one hundred percent in-line material evaluation, as well as evaluation and testing in a laboratory environment.

SUMMARY OF THE INVENTION

Apparatus for measuring one or more preselected properties of test pieces in accordance with a presently preferred embodiment of the invention includes a variable frequency oscillator for providing a periodic signal, and a test coil arrangement for applying the periodic signal to a test piece to generate eddy currents therein. A test signal is developed in response to eddy currents induced in the test piece and fed to a microprocessor-based digital controller. The digital controller is coupled to the oscillator for generating the periodic oscillator signal at successive first and second test frequencies. At least two harmonic components of the test signal are separated from each other by the digital controller at each test frequency. A plurality of constants empirically relating amplitude and phase characteristics of the harmonics to the desired material properties are prestored in the digital processor, and are employed in conjunction with amplitude and phase information of the separated harmonic components during a test operation using linear regression techniques for determining desired properties of the test pieces.

Thus, one specific aspect of the present invention contemplates a method of measuring a preselected property of a test piece, such as a metallurgical property of a ferromagnetic test piece, that comprises the step of providing a plurality of sample pieces having differing predetermined values of the desired preselected property. Each of the sample pieces is subjected in turn to the periodic signal to induce eddy currents therein, and a test signal is developed in response to eddy currents in each of the sample pieces. Harmonic components of the test signals are separated for each of the sample pieces in turn to develop amplitude and phase information related to at least two harmonic components for each sample piece. The predetermined numerical values of the sample pieces, and the amplitude and phase information for each harmonic component and each test piece are then analyzed using otherwise conventional linear regression techniques, preferably forward and backward step-wise multiple regression techniques, empirically to derive a plurality of constants that relate amplitude and phase information of the multiple harmonic components to the desired property of the sample pieces. These constants are then stored in memory and employed during a test operation for measuring or predicting the desired property of a test piece. Most preferably, both the calibration and measurement operations are carried out at multiple differing signal frequencies.

In accordance with another specific aspect of the present invention, frequency and/or amplitude of the periodic signal applied to the test piece is closely monitored and changed only when the instantaneous amplitude of the periodic signal (as distinguished from the RMS amplitude or peak-to-peak amplitude) is substantially equal to zero. This is accomplished in the preferred embodiment of the invention by applying the periodic signal to a zero-crossing detector, which enables modification of the signal frequency and/or peak signal amplitude when the voltage applied to the test coil crosses zero volts. In this way, ringing and generation of spurious harmonics in the test coil secondary are avoided, enhancing both speed and accuracy of the measurement.

In accordance with a further specific aspect of the presently preferred embodiment of the invention, the oscillator for generating the periodic signal applied to the test piece takes the form of a digital oscillator that includes facility for enhanced control and resolution of test frequency by the control microprocessor over an extended frequency range. The oscillator in the preferred embodiment of the invention comprises a digital counter having a binary bit-parallel output and a clock input. A pulsed signal is applied to the count input of the counter at constant frequency greater than desired oscillator output frequency, such that the bit-parallel counter output varies monotonically—i.e., in a stepwise ramp signal format—as a function of the count input. A look-up table has an address input coupled to the counter output, a bit-parallel data output, and addressable prestored data that converts the counter output address signal into a digital replica of the desired oscillator output waveform. A digital-to-analog converter has a bit-parallel input connected to the data output of the look-up table, and an output for providing a periodic analog signal of preselected waveform corresponding to that stored in the look-up table. Preferably, the stored waveform is of pure sinusoidal configuration. The pulsed signal to the counter input is provided by a high frequency clock and a phase-locked loop that includes at least one programmable divider connected to the control microprocessor for selectively varying the frequency of the oscillator output signal.

As previously noted, the presently preferred embodiment of the invention contemplates employment of microprocessor-based control electronics and digitally controlled multiple test frequencies. The test signal generated by eddy currents in the test piece is directed to an analog-to-digital converter for sampling and storing in the control microprocessor at predetermined fractional increments synchronized with each cycle of the periodic signal applied to the workpiece. A problem therefore arises when the test frequency is of sufficient magnitude that the fractional sampling increments exceed the capabilities of the input electronics to sample and store digital information. In accordance with yet another specific aspect of the presently preferred embodiment of the invention, the test signal is sampled at an integral number of increments greater than the minimum sampling time of the input electronics over a plurality of periodic signal cycles. After a number of signal cycles, all of the desired information is stored in processor memory, and is rearranged or interleaved to correspond with the desired sequence of fractional increments. Where sampling is desired at an even number of increments in each cycle, actual sampling is accomplished at odd integral multiples of desired sampling increments so that the sample points automatically vary on each successive signal cycle to include all desired sampling points after multiple signal cycles.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF PREFERRED EMBODIMENT

Figure 1:
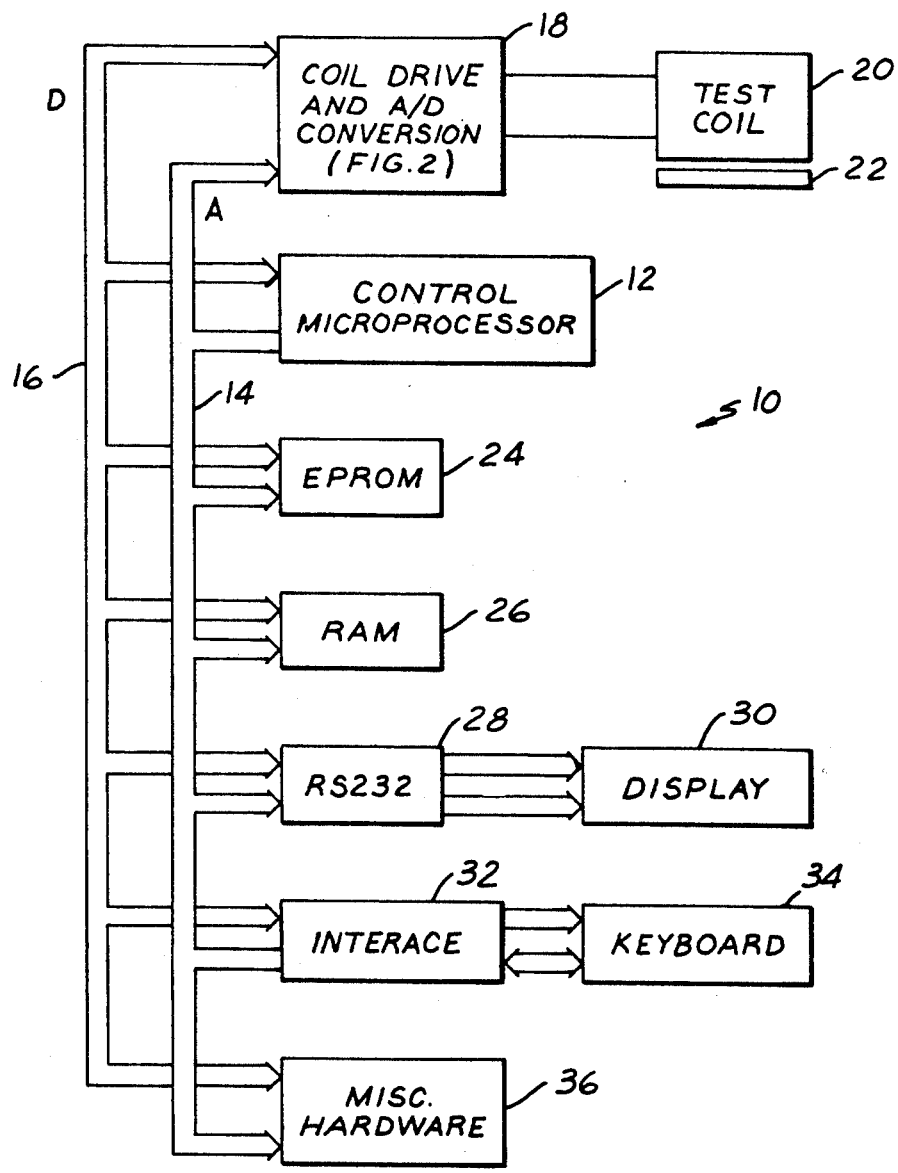
FIG. 1 is a functional block diagram of a presently preferred embodiment of test apparatus in accordance with the invention.

FIG. 1 illustrates apparatus 10 in accordance with a presently preferred embodiment of the invention as comprising a control microprocessor 12 coupled by an address bus 14 and a data bus 16 to the remainder of the apparatus electronics. Coil drive and a/d conversion electronics 18 (FIGS. 1 and 2) are controlled by microprocessor 12 to apply a periodic signal to a test coil 20 positioned adjacent to a test part 22 to generate eddy currents therein, and to feed information derived by the test coil assembly from the induced eddy currents back to the control microprocessor. Control microprocessor 12 is also connected by buses 14, 16 to an EPROM 24 having control programming prestored therein, to a RAM 26 for storing measurement constants and other transient data, through an RS232 interface 28 to a suitable device 30 for displaying operating conditions and test results to an operator, through an interface 32 to a keyboard 34 for entry of data and control information, and to miscellaneous hardware 36 such as a printer, an apparatus for sorting test pieces based upon test results, etc. Preferably all control electronics 12, 18, 24–28 and 32 are housed within a protective enclosure having display 30 and keyboard 34 on the front panel, and having suitable leads or cables for connection to coil 20 and hardware 36. Coil 20 may be of any geometry suitable for the test pieces 22. Test pieces 22 may be presented in sequence to coil 20 by any suitable transfer device.

Figure 4:
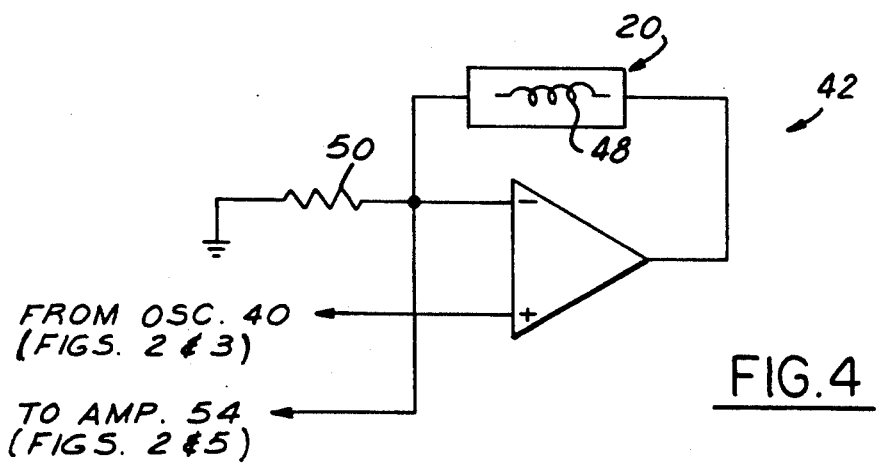
FIG. 4 is a schematic diagram of the current drive amplifier in FIG. 2.
Figure 2:
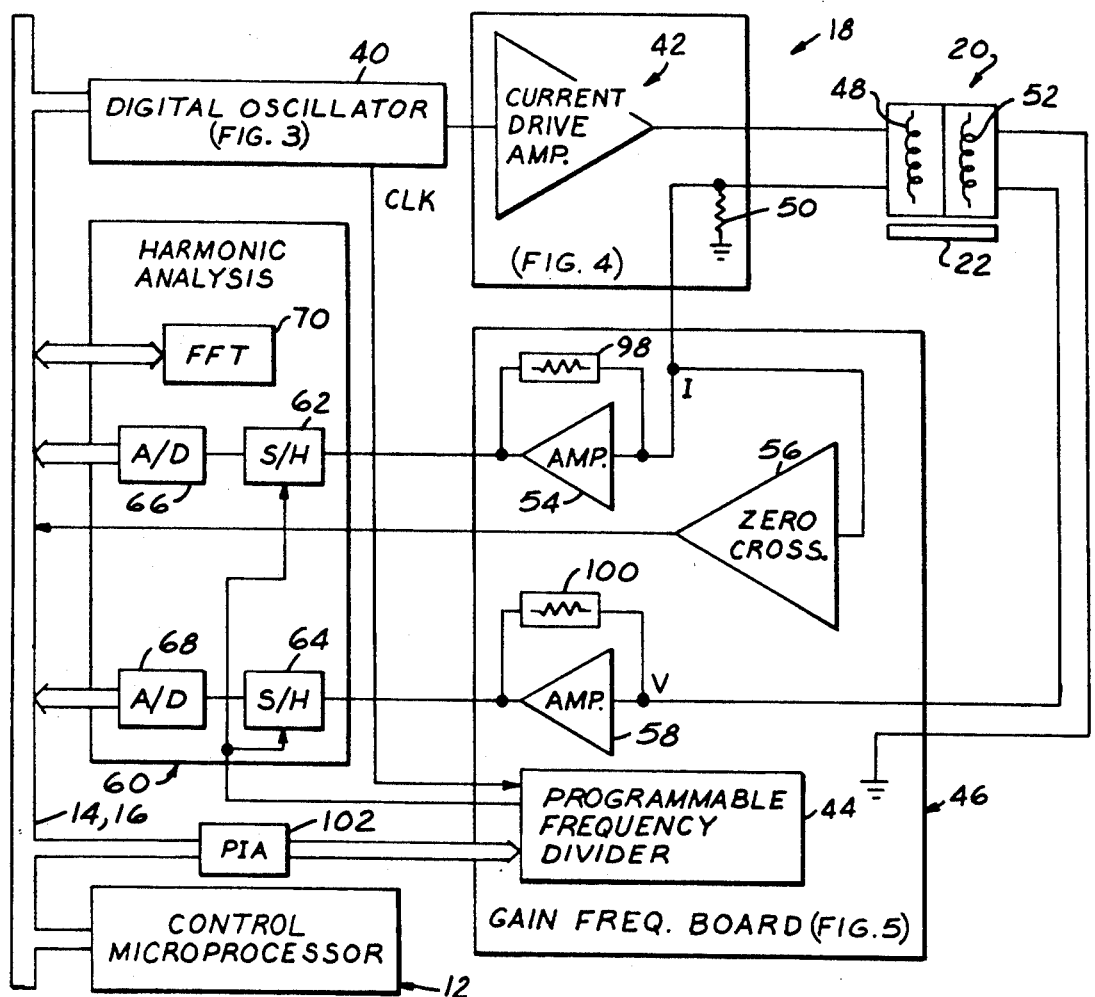
FIG. 2 is a fragmentary functional block diagram of the apparatus of FIG. 1 showing the coil drive and a/d conversion electronics in greater detail.
Figure 5:
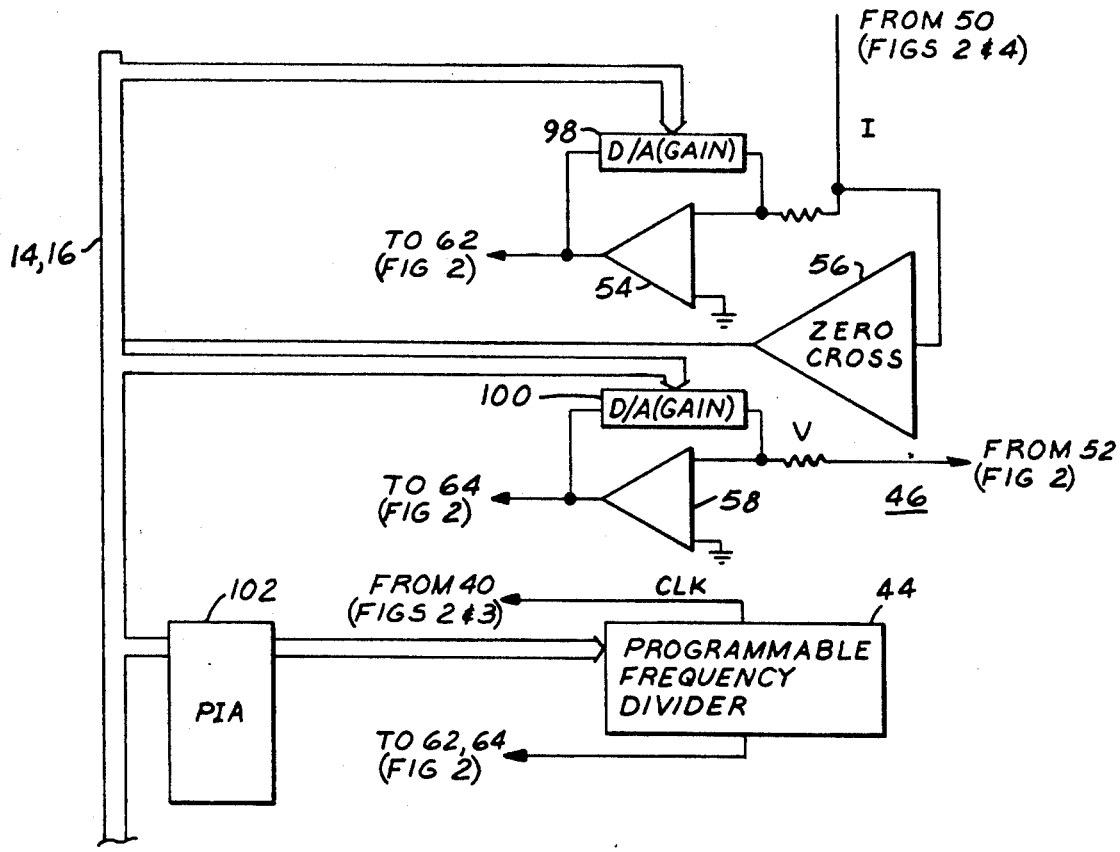
FIG. 5 is a detailed functional block diagram of the gain and sampling frequency control electronics in FIG. 2.

FIG. 2 illustrates coil drive and a/d conversion electronics 18 in greater detail. A digital oscillator 40 (FIGS. 2 and 3) provides a highly stable low harmonic sine wave to a current drive amplifier 42 (FIGS. 2 and 4). A clock signal CLK precisely synchronized to the cycle of the sine wave is also fed by oscillator 40 to a programmable frequency divider 44 within a gain and sampling frequency electronics package 46 (FIGS. 2 and 5). Amplifier 42 converts the sine wave input from oscillator 40 to a current applied to the primary coil 48 of coil assembly 20. Amplifier 42 (FIGS. 2 and 4) is configured as a current driver having primary coil 48 connected in the amplifier feedback path. The primary coil current is also fed to a resistor 50, which thus provides a signal I indicative of amplitude and phase of current applied to the coil assembly. As is well known in the art, the magnetic field generated by the periodic signal applied to primary coil 48 induces eddy currents in adjacently positioned test piece 22, which in turn induce current in the secondary coil 52 of coil assembly 20 as a function of amplitude and phase of the eddy currents.

Within gain and frequency control electronics 46 (FIGS. 2 and 5), the signal I indicative of current applied to primary coil 48 is fed to the inputs of a digitally controlled amplifier 54 and a zero-crossing detector 56. In the same way, the signal V indicative of voltage developed at secondary coil 52 is applied to the input of a digitally controlled amplifier 58. The gain stages 98, 100 of amplifiers 54, 58 are connected to microprocessor 12 by buses 14, 16. The outputs of amplifiers 54, 58 are connected within a harmonic analysis package 60 to the inputs of corresponding sample-and-hold (s/h) circuits 62, 64. The outputs of s/h circuit 62, 64 are fed to corresponding a/d converters 66, 68, and thence to microprocessor 12 by data bus 16. Microprocessor 12 is also connected by buses 14, 16 within harmonic analysis package 60 to a digital processor 70 that is preprogrammed and dedicated to performing fast fourier transform (FFT) analysis of input signal data. FFT analyzer may be any suitable construction and programming available in the art. FFT analyzer returns data to microprocessor 12 indicative of amplitude and phase information of the separated harmonic signal components. The s/h circuits 62, 64 receive sample control signals from programmable frequency divider 44. Divider 44 is connected to microprocessor 12 by buses 14, 16 and an interface adapter 102 (FIG. 5).

Figure 3:
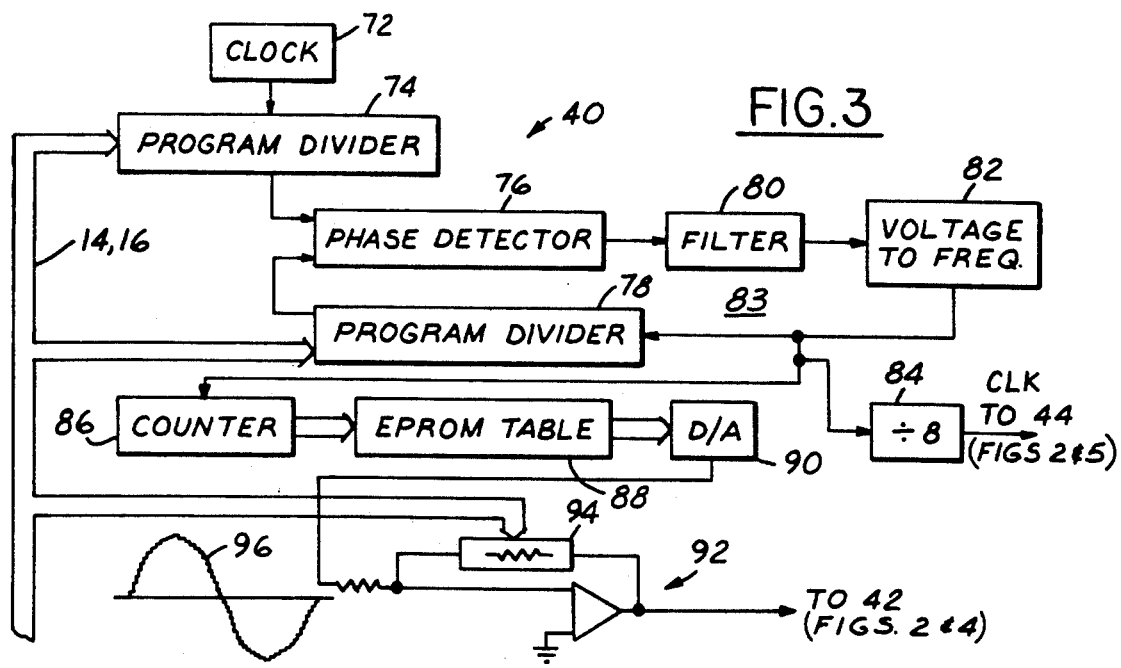
FIG. 3 is a detailed functional block diagram of the digital oscillator in FIG. 2.

FIG. 3 illustrates digital oscillator 40 in greater detail. A stable high frequency crystal clock 72 provides a pulsed signal to a first programmable divider 74. The output of divider 74 is fed to a phase detector 76, which receives a second input from a second programmable divider 78. The output of phase detector 76 is fed through a filter 80 to a voltage-to-frequency converter 82. The output of converter 82 is fed as an input to programmable divider 78. Thus, divider 78, phase detector 76, filter 80 and converter 82 form a phase-locked loop 83 for providing at converter 82 an output signal at frequency controlled by dividers 74, 78. Dividers 74, 78 are connected by buses 14, 16 to control microprocessor 12 (FIGS. 1 and 2) for controlling frequency of operation of oscillator 40. The output of converter 82, which forms the output of loop 83, is fed to a divider 84 for dividing the frequency of the converter output by some preselected integer to provide the clock input CLK to programmable frequency divider 44 (FIGS. 2 and 5). In a working embodiment of the present invention, phase-locked loop 83 is configured to provide an output frequency equal to 256 times the desired output frequency from oscillator 40. Divider 84 is configured as a divide-by-eight divider, so as to provide to programmable frequency divider 44 thirty-two uniformly spaced clock pulses that are highly synchronized with the current drive sine wave, and thus effectively divide each sine wave cycle into thirty-two equal fractional increments.

The output of converter 82 is also connected to the count input of a counter 86. The bit-parallel output of counter 86 is fed to the address input of an EPROM look-up table 88. The data output of table 88 is fed through a d/a converter 90 to the input of a digitally controlled amplifier 92. The gain control 94 of amplifier 92 is coupled by buses 14, 16 to microprocessor 12 for controlling gain of amplifier 92. Table 88 is preprogrammed with sequentially addressable data for converting the address input from counter 86 to the desired oscillator output waveform. Preferably, this waveform is a pure sine wave. Thus, table 88 is programmed to convert the monotonically increasing stepped ramp output of counter 86 into 256 uniformly spaced steps of a replica sine wave 96, which is fed by amplifier 92 at controlled gain to the output of current amplifier 42 (FIGS. 2 and 4). Programmable amplifier 92 provides adjustments necessary for multiple frequency operation, and for variations caused by different designs and geometries of coils 20. As will be described hereinafter, amplifier 92 is also employed in conjunction with zero-crossing detector 56 (FIGS. 2 and 5) to provide transient free information at the output of secondary coil 52.

In operation of apparatus 10, a pure low-harmonic sine wave is generated by oscillator 40 and applied by current drive amplifier 42 to primary coil 48. This sine wave excitation current produces eddy currents in test part 22, which in turn produce a test signal in secondary coil 52. Amplitude and phase of the harmonic components of this test signal in secondary coil 52 are related to the metallurgical properties of test piece 22. Excitation current signal I and secondary voltage signal V are each sampled at thirty-two fractional increments of the excitation signal cycle. The sampled signal is data fed by microprocessor 12 to FFT analyzer 70, which separates the harmonic components of the respective signals. Since signal I is a pure sine wave, only the fundamental or first harmonic component is present. The odd harmonic components of secondary test signal V are separated by analyzer 70 to identify amplitude and phase information related to the respective components. In the above-noted working embodiment of the invention, the first (fundamental), third and fifth harmonics of secondary test signal V are separated by analyzer 70 and identified by descriptors that contain amplitude and phase information related to each harmonic. These descriptors preferably take the form of sine and cosine descriptors that define amplitude and phase of each harmonic. These descriptors are transmitted to microprocessor 12 and stored in RAM 26 (FIG. 1) for further analysis and processing, as will be described.

In accordance with one feature of the preferred embodiment of the invention, following implementation of the fast fourier transform analysis, the amplitude information of the first, third and fifth harmonics of secondary signal V is divided by amplitude of the primary signal I. This feature effectively normalizes the test signal data against variations in the periodic primary signal caused by temperature or other conditions. The normalized amplitude and phase information associated with the first, third and fifth harmonics of the test signal thus provides six descriptors for analysis of the metallurgical properties of test piece 22. Following analysis and storage of these descriptors, microprocessor 12 changes the frequency of excitation of oscillator 40, whereupon new readings of the primary and secondary coil signals are taken, analyzed for harmonic content, and normalized as previously described. This process is repeated for a desired number of test frequencies. In the subject working embodiment of the invention, four test frequencies are employed, thus yielding a total of twenty-four descriptors for each test piece—i.e., two descriptors respectively indicative of amplitude and phase of each harmonic component times three harmonic components per test frequency times four test frequencies.

These twenty-four descriptors are then weighted in accordance with the predetermined contribution of each descriptor in determining the desired property. The weighting factor for each descriptor may be determined in accordance with any number of conventional statistical techniques. Most preferably, and in the subject working embodiment of the invention, forward and backward step-wise multiple linear regression techniques are employed, as will be described. The derived harmonic information is thus employed in linear regression equation of the following general form: Equation $D = C_1F_1 + C_2F_2 + C_3F_3 \ldots + C_{24}F_{24}$, where $C_N$ is the corresponding previously-determined regression coefficient for descriptors $N = 1$ to 24, $F_N$ is the harmonic information (sine and cosine) descriptors for $N = 1$ to 24, and D is the corresponding property to be measured. The numerical valve D of the desired property may then be displayed at 30 (FIG. 1) to an operator, or employed at 36 to sort test pieces. The latter use may involve comparison to prespecified values or a prespecified range for sorting acceptable from unacceptable parts. For example, the property of interest may be degree of heat treatment of the test pieces, and microprocessor 12 may be preprogrammed to operate a reject chute or the like to separate parts having less than 90% heat treatment.

The regression coefficients $C_1$ to $C_{24}$ in the above equation are empirically predetermined. For example, assume that apparatus 10 is to be employed for determining hardness of test pieces 22. A plurality of sample pieces are supplied having differing hardness values $D_1$ through $D_M$. Each sample piece is positioned adjacent to coil assembly 20, the coil assembly is driven at suitable frequency, current and voltage readings I,V are taken, and corresponding harmonic descriptors are calculated. This process is repeated at several suitable test frequencies, and for each of the sample pieces in turn. The resulting data constitutes a linear array of known hardness values $D_1$ through $D_M$, a matrix array of harmonic descriptors $F_{11}$ through $F_{M24}$, and a matrix array of unknown constants $C_1$ through $C_{24}$. This information is then analyzed in accordance with conventional forward and backward step-wise multiple regression techniques to identify values for constants $C_1$ through $C_{24}$ that yield highest correlation of harmonic descriptors to known hardness values $D_1$ through $D_M$. The values of some of these constants may, of course, be negative or zero. Test frequencies may be selected to yield highest data correlation. (Indeed, less than three frequencies may be employed in particular circumstances, and more test frequencies may be employed where necessary.) The calculated values $C_1$ through $C_{24}$ of the regression constants are then loaded into RAM 26 (FIG. 1) for use during subsequent measurement cycles.

It should be noted, in this respect, that the invention is by no means limited to measurement of one property in a given workpiece. Thus, the same M sample pieces may have differing case depths $E_1$ through $E_M$, which may be employed in the same matrix analysis with the same harmonic descriptors to derive corresponding constants $C'_1$ through $C'_{24}$ for relating the same harmonic descriptors to case depth. Constants $C'_1$ through $C'_{24}$ for case depth may, of course, vary radically from constants $C_1$ through $C_{24}$ for hardness. The invention thus provides a powerful and versatile tool for analyzing one or multiple metallurgical properties of test pieces. Test frequencies and regression constants that yield best data correlation are stored in RAM 26 for further use. By way of example, only three test frequencies (100,200 and 400 Hz) have been found necessary and suitable for analyzing case depth of automotive camshafts.

With the regression constants empirically determined and loaded into RAM 26 (FIG. 1) as described, apparatus 10 is ready for a test sequence. Upon initiation of a test operation, oscillator gain control 94 (FIG. 3) is set at a low or standby level, and dividers 74, 78 are set by microprocessor 12 to the first test frequency. Upon occurrence of a zero-crossing of excitation signal I, detected by zero-crossing detector 56 (FIGS. 2 and 5), microprocessor 12 resets gain control 94 to the first test amplitude. Gains 98, 100 (FIGS. 2 and 5) are likewise set at levels empirically predetermined to correspond with the probe configuration, test frequency and other variables being employed. Frequency divider 44 is set to optimize data gathering, as will be described in conjunction with FIG. 6. Upon occurrence of the next zero-crossing at detector 56, the current and voltage signals are sampled at thirty-two fractional increments of each cycle over a preset number of cycles, and then averaged. The averaged data so obtained is then fed to FFT analyzer 70 for separation of harmonic components. Upon detection of a zero-crossing, gain 94 is reduced to the standby level. The test frequency is changed at the next zero crossing. Signal amplitude is then increased at the next signal crossing, and new test signal data is sampled and stored.

In the meantime, FFT analyzer separates the first, third and fifth harmonic components of sampled and averaged signals I and V. This process is repeated for each of the third and fourth test frequencies and amplitudes. After twenty-four descriptors are obtained and stored, the desired property or properties of the test piece are calculated, displayed at 30 and/or transmitted to miscellaneous hardware 36 (FIG. 1) for printing or operation of a part sorting device.

Figure 6:
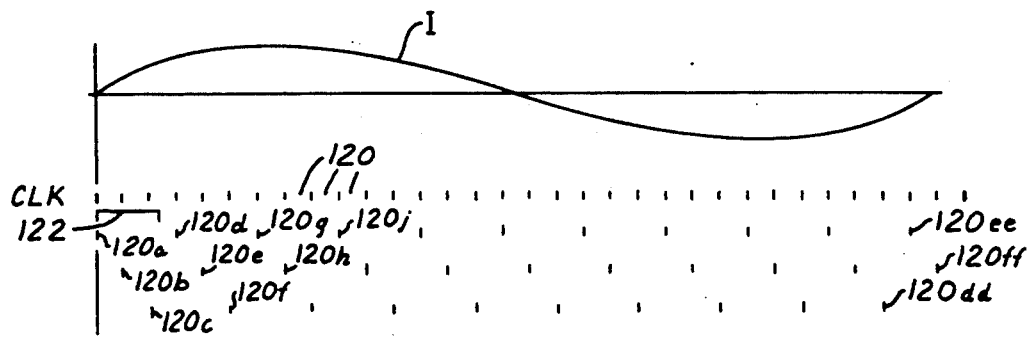
FIG. 6 is a graphic illustration useful in describing operation of the sampling frequency control electronics in FIGS. 2 and 5.

Optimized data gathering implemented by programmable divider 44 (FIGS. 2 and 5) is graphically illustrated in FIG. 6, which illustrates various signals on a common time base. Clock signals CLK provided by oscillator 40 to divider 44 are closely synchronized to each cycle of drive current I and effectively divide each cycle into thirty-two equal fractional increments 120. The time duration of each of the thirty-two increments 120 is thus an inverse function of signal frequency. S/h circuits 62, 64 and a/d converters 66, 68 are characterized by a minimum sample-and-hold cycle time 122 in which data can be sampled, converted and loaded by microprocessor 12 into RAM 26 (FIG. 1). As long as the frequency of drive current I is sufficiently low, and the drive current wavelength is correspondingly sufficiently high, the fractional time duration of the sampling intervals 120 will exceed minimum sampling time 122. However, when a higher test frequency is employed, so that sampling increment time duration 120 is less than minimum sampling time 122 as illustrated in FIG. 6, programmable frequency divider 44 is operated by control microprocessor 12 to optimize data gathering over a number of periodic signal cycles.

More particularly, and referring to FIG. 6, it will be observed that, in the example therein illustrated, minimum sampling time 122 is greater than twice the interval time duration 120. Microprocessor 12 programs frequency divider 44 to initiate sampling of the signal I, V at circuits 62, 64 at the minimum odd integral number of sampling intervals 120 that exceeds the minimum sampling time 122. Thus, in the illustration of FIG. 6, in which minimum sampling time 122 exceeds two sampling intervals 120, programmable divider 44 is set by microprocessor 12 to divide incoming signal CLK from oscillator 40 by three. In this way, the incoming signals I and V are sampled at every third sample time, over three successive cycles. That is, in the first cycle, the incoming signals are sampled at times 120a, 120d, 120g, 120j . . . 120ee. On the next cycle, sampling takes place at times 120b, 120e, 120h . . . 120ff. Likewise, on the third cycle, sampling takes place at times 120c, 120f . . . 120dd. Thus, over three successive cycles, all thirty-two samples are obtained Note that the use of an odd number of sampling intervals automatically obtains correct sampling over a corresponding number of successive cycles. That is, the third sample count from time 120ee in the first cycle is time 120b in the second cycle, and the third sample count from time 120ff in the second cycle is time 120c in the third cycle. Following the third cycle, the sampled data is complete, but out of order in RAM 26. Microprocessor 12 automatically rearranges or interleaves the sampled data in the correct order prior to transmission to FFT analyzer 70 (FIG. 2) for harmonic component analysis and separation.

We claim:

1. Apparatus for measuring a preselected property of a test piece that comprises:
    oscillator means for providing a periodic signal, including means for selectively varying frequency of said periodic signal,
    means for applying said periodic signal to a test piece to generate eddy currents therein,
    means responsive to said eddy currents generated in the test piece for providing a test signal, which is indicative of said preselected property, and
    digital processing means including means coupled to said oscillator means for generating said periodic signal at said oscillator means at successive first and second differing test frequencies, means responsive to said test signal at each said test frequency for separating at least two harmonic components of said test signal, means responsive to amplitude and phase information of said harmonic components at both said frequencies for determining said preselected property of the test piece, and means for compensating said test signal against variations in said periodic signal by dividing amplitude of said test signal by amplitude of said periodic signal.

2. The apparatus set forth in claim 1 wherein said digital processing means further includes means for storing a plurality of constants empirically relating amplitude and phase characteristics of said harmonics to said preselected property, and wherein said property-determining means comprises means for determining said property as a combined function of said constants and said amplitude and phase information.

3. The apparatus set forth in claim 1 further comprising means responsive to said periodic signal for indicating when said periodic signal crosses zero voltage level, and wherein said oscillator-coupled means includes means responsive to said zero-crossing indication for switching said oscillator between said first and second frequencies.

4. The apparatus set forth in claim 1 wherein said oscillator means comprises a digital oscillator including a digital counter having an output and a count input, means for providing a pulsed signal to said count input a frequency exceeding a desired test frequency of said periodic signal such that said counter output varies a function of said pulsed signal, d/a converter means and look-up table means having an address input coupled to said counter output and a data output coupled to said d/a converter means, said look-up table means having prestored therein data that converts varying digital input from said counter into a sinusoidal output at said d/a converter means.

5. The apparatus set forth in claim 1 wherein said oscillator means includes means for providing said periodic signal alternately at a standby voltage level and at a measurement voltage level greater than said standby voltage level, and wherein said apparatus further comprises means responsive to said periodic signal and coupled to said oscillator means for switching said oscillator means between said standby and measurement voltage levels when instantaneous amplitude of said periodic signal is substantially equal to zero voltage level.

6. The apparatus set forth in claim 1 further comprising means responsive to said periodic signal for indicating when said periodic signal crosses zero voltage level; and wherein said digital processing means further comprises means coupled to said oscillator means for generating said periodic signal at first and second test amplitudes, and means responsive to said zero-crossing indication for switching at said oscillator between said first and second test amplitudes.

7. The apparatus set forth in claim 6 wherein said oscillator means includes an output amplifier having digitally controlled gain coupled to said digital processing means.

8. The apparatus set forth in claim 1 wherein said digital processing means includes a/d conversion means for sampling said signal at predetermined fractional increments of each cycle of said periodic signal.

9. The apparatus set forth in claim 8 wherein said a/d conversion means is characterized by a minimized sampling time; and wherein said digital processing means further includes means responsive to said minimum sampling time exceeding time intervals between said fractional increments for sampling said test signal at an integral number of said increments exceeding said minimum sampling time over a plurality of periodic signal cycles and interleaving the sampled signals in order corresponding to said fractional increments.

10. The apparatus set forth in claim 1 wherein said digital processing means includes means for storing a plurality of constants empirically relating said amplitude and phase information to said preselected property, and means for determining said preselected property of said test piece as a function of said constants and said amplitude and phase information.

11. The apparatus set forth in claim 10 wherein said oscillator means comprises means for operating said signal at a plurality of differing frequencies; wherein said component-separating means is constructed to develop said amplitude and phase information for each said component at each said frequency; and wherein said digital processing means includes means for storing constants empirically relating said amplitude and phase information to said property at each said frequency, and means for determining said property as a combined function of said constants and said information at all of said frequencies.

12. The apparatus set forth in claim 1 further comprising means for monitoring amplitude of said periodic signal, and means for switching said periodic signal between said first and second frequencies when instantaneous amplitude of said periodic signal is substantially equal to zero.

13. The apparatus set forth in claim 12 wherein said amplitude-monitoring mans comprises a zero-crossing detector.

14. The apparatus set forth in claim 12 wherein said oscillator means comprises a variable frequency oscillator and means for changing frequency of said oscillator when instantaneous amplitude of said periodic signal is substantially equal to zero.

15. The apparatus set forth in claim 12 wherein said oscillator means has variable peak output amplitude, and means for changing peak output amplitude of said oscillator means when instantaneous amplitude of said periodic signal is substantially equal to zero.

16. The apparatus set forth in claim 15 wherein said oscillator means includes an output amplifier having variable gain control, and wherein said amplitude-changing means comprises means for changing said gain control when instantaneous amplitude of said periodic signal is substantially equal to zero.

17. A digital oscillator for supplying a periodic analog signal of preselected waveform and variable frequency comprising:
a digital counter having a binary bit-parallel output and a clock input,
means for providing a pulsed signal to said count input at constant frequency greater than desired oscillator output frequency, such that said bit-parallel counter output varies as a stepped monotonic function of said count input,
look-up table means having an address input coupled to said counter output, a bit-parallel data output and addressable prestored data that converts said counter output to a digital replica of said preselected waveform, and
d/a converter means having a bit-parallel input connected to said data output and a output for providing said analog signal.

18. The oscillator set forth in claim 17 wherein said pulsed signal-providing means comprises a high frequency clock and programmable divider means having a signal input coupled to said clock and a control input for selectively varying frequency of said pulsed signals to said counter and thereby varying output frequency of said oscillator.

19. The oscillator set forth in claim 18 wherein said programmable divider means comprises a phase-locked loop.

20. The oscillator set forth in claim 19 wherein said preselected waveform comprises a sinusoidal waveform.

21. Apparatus for measuring a preselected property of a test piece that comprises:
oscillator means for providing a periodic signal, including means for selectively varying frequency of said periodic signal,
means for applying said periodic signal to a test piece to generate eddy currents therein,
means responsive to said eddy currents generated in the test piece for providing a test signal, which is indicative of said preselected property, and
digital processing means including means coupled to said oscillator means for generating said periodic signal at said oscillator means at successive first and second differing test frequencies, means responsive to said test signal at each said test frequency for separating at least two harmonic components of said test signal, and means responsive to amplitude and phase information of said harmonic components at both said frequencies for determining said preselected property of the test piece,
said oscillator means comprising a digital oscillator including a digital counter having an output and a count input, means for providing a pulsed signal to said count input at a frequency exceeding a desired test frequency of said periodic signal such that said counter output varies as a function of said pulsed signal, d/a converter means, and loop-up table means having an address input coupled to said counter output and a data output coupled to said d/a converter means, said look-up table having prestored therein data that converts varying digital input firm said counter into a sinusoidal output at said d/a converter means.

22. The apparatus set forth in claim 21 wherein said pulsed signal-providing means comprises a high frequency clock and programmable divider means having a signal input coupled to said clock and a control input coupled to said digital processing means for selectively varying frequency of said pulsed signals to said counter and thereby varying output frequency of said oscillator.

23. The apparatus set forth in claim 22 wherein said programmable divider means comprises a phase-locked loop.

* * * * *